(12) United States Patent
Steffier

(10) Patent No.: US 6,455,033 B1
(45) Date of Patent: Sep. 24, 2002

(54) ARTIFICIAL NAILS

(75) Inventor: Larry Steffier, Cherry Hill, NJ (US)

(73) Assignee: Mycone Dental Corp., Cherry Hill, NJ (US)

( * ) Notice: Subject to any disclaimer, the term of this patent is extended or adjusted under 35 U.S.C. 154(b) by 0 days.

(21) Appl. No.: 09/362,847

(22) Filed: Jul. 28, 1999

(51) Int. Cl.[7] .............................. A61K 7/04; A61K 7/00
(52) U.S. Cl. .......................................... 424/61; 424/401
(58) Field of Search .................................. 424/61, 401

(56) References Cited

U.S. PATENT DOCUMENTS 5,523,076 A * 6/1996 Schoon ........................ 424/61
5,965,147 A * 10/1999 Steffier ........................ 424/401
5,968,986 A * 10/1999 Dyer ............................ 514/643

* cited by examiner

Primary Examiner—Thurman K. Page
Assistant Examiner—S. Tran
(74) Attorney, Agent, or Firm—Dilworth Paxson LLP

(57) ABSTRACT

A composition useful for artificial nails, artificial nail preparations, and nail primers having resistance to greenies comprising a liquid component comprising one or more polymerizable acrylic monomers, a solid or gel component comprised of polymerization initiator catalyst and a polymer of one or more acrylic monomers, and one or more antimicrobial compounds. A method of preparing the composition, a method of forming an artificial human nail, and an artificial human nail formed from each composition are also disclosed.

19 Claims, No Drawings

ARTIFICIAL NAILS

BACKGROUND OF THE INVENTION

1. Field of the Invention

The present invention is directed generally to artificial human nails.

2. Description of the Prior Art

The use of artificial human nails has become very prevalent, especially among fashion conscious women. There are many nail salons, both independent and affiliated with beauty shops, where trained professionals are available to apply artificial nails. There are also many systems for do-it-yourself application of artificial nails. Various synthetic polymers have been proposed for artificial human nails. In practice, most artificial nail systems are comprised of acrylic polymers, monomers, UV curable acrylate oligomers (gels), cyanoacrylates, and/or polyalkyl cyanoacrylates in one form or another, along with catalysts such as organic peroxides and toluidine, UV initiators, accelerators, pigments, secondary polymers, and flow modifiers. In this art, ease of application, fast and strong hardening, wearer comfort, durability, and cosmetic appearance have been the primary objectives in the past, and several compositions and methods have been proposed and used to address those objectives.

Among the artificial nail systems currently on the market are some which comprise a monomer system, known as the liquid component, and a solid powdered polymer component which contains the catalyst, known as the powder or solid or catalyst or accelerator. For example, Montgomery U.S. Pat. No. 5,098,696 assigned to REM Systems, Inc., discloses a composition which comprises methoxyethoxyethyl methacrylate, ethylene glycol dimethacrylate, and hydroxyethyl methacrylate as the monomers in the liquid component, and a polymeric powder portion comprised of polyethyl methacrylate with benzoyl peroxide ground on the surface of the powder.

As is well known in the art, such as taught in U.S. Pat. No. 5,738,843 to Montgomery, which is incorporated by reference, typical artificial fingernails are constructed with a liquid monomer component and a polymeric powder composition, which, upon being admixed at the time of use, harden to a fused polymer in the shape of an artificial fingernail and/or decorative coating in from between about 60 seconds to about 180 seconds, at ambient temperatures.

In addition to the above components, the liquid component may optionally contain a polymerization inhibitor such as butylate hydroxy toluene or the methyl ether of hydroquinone (MEHQ) to prevent premature reaction of the methacrylate monomers and to assure adequate shelf life. Light stabilizers, such as 2-hydroxy-4-methoxy-benzophenone can be included in the liquid component portion to prevent light-activated polymerization and to give the resulting polymeric fingernail that is formed resistance to yellowing the ultraviolet light. Finally, auxiliary components such as dyes and hydroxy methacrylate monomers may be included so as to modify color and post-cure properties, respectively.

Schoon U.S. Pat. No. 5,523,076 assigned to Creative Nail Design, Inc., discloses a system wherein the monomer component is comprised of alkyl methacrylate and hydroxyalkyl methacrylate in a weight ratio of 2–20:1 and a powdered polymer component containing the polymerization (cross-linking) catalyst such as benzoyl peroxide. The powdered polymer catalyst component is added to the liquid at the time of application, and polymerization of the liquid monomers takes place at room temperature.

Among the acrylic systems are those which include acrylate oligomers such as urethane acrylate oligomers, urethane methacrylate oligomer, epoxy acrylate oligomer, polyester acrylate oligomer, aromatic acid oligomer, alkylcyanoacrylate, polyalkylcyanoacrylate, and epoxy methacrylate oligomers, and the like, which can be used in combination with polyfunctional acrylates or methacrylates such as ethylene glycol diacrylate and alkoxy acrylates or methacrylates.

Some products are used with a primer such as methacrylic acid, which is applied to the human nail surface prior to application of the monomer and catalyst powder. Other systems, such as the Montgomery systems, are designed for use without primer. Fingernail primers can be based on acrylic monomers or derivatives of acrylic monomers. Both methacrylic acid and unsaturated carboxylic derivatives such as those described in U.S. Pat. No. 4,863,993 as well as solvents and modified solvent mixtures such as those described in U.S. Pat. No. 4,766,005 are also contemplated as useful for inhibition of microbial growth and covered in this patent.

Problems with artificial nail systems, especially with those systems which do not use primer, have been noted in the art. More specifically, a very serious problem involving microbial growth, mostly involving fungus or bacteria development in, around, or under the artificial nail, known in the art as "greenies," has occurred with such systems. Greenies is a condition which can cause onychomycosis.

Since greenies are not only unsightly and uncomfortable, but can be very dangerous, nail technicians and others who work with artificial nail systems have tried many methods to prevent greenies, including sterile procedures incorporating lint free cuticle removal. There are a number of recognized anti-fungal treatments for treating onychomycosis or greenies, for example scraping or drilling into the nail to expose an infected area, using a nail permeable medication which is topically applied such as disclosed in U.S. Pat. No. 5,840,283 wherein a proteolytic enzyme component facilitates permeation through the nail, and allowing the medication to directly contact the fungus growth area. Another example of a treatment method for greenies is disclosed in U.S. Pat. No. 5,464,610 in which salicylic acid or a salt ester solution is topically administered in a plaster preparation.

There have been several attempts in fields other than the artificial nail field to combine anti-fungal agents with polymers, for example use of a surface-modified denture resin, manufactured from poly(methyl-methacrylate), which carries a candidacidal protein (histatin 5). As the candidacidal protein is desorbed by the surface of the polymer over time, a reduction in surrounding fungus cells was observed. Edgarton, M. et al., *Surface-modified poly(methyl methacrylate) enhances adsorption and retains anticandidal activities of salivary histatin 5*. *J. Biomedical Material Research*, Vol 29. No. 10 pg 1277–86. Further examples using different polymers and anti-fungal agents are disclosed in U.S. Pat. No. 5,674,934 entitled "Reversible and Irreversible Water-based Coatings," Japanese Pat. No. 07309755 entitled "Cataplasm of Antifungal Agent" and European Patent No. 96-33 0516141 entitled "Pharmaceutical Controlled Release Composition with Bioadhesive Properties."

However, the field of artificial nails is different than the aforementioned fields in which antimicrobial polymers have been used. In this field, color, stability, shelf life, ease of applicability, speed of hardening, durability, strength, and adhesion to natural nail surface are among the several concerns which must be addressed in design of a commercially acceptable artificial nail system. To date, no one has proposed an artificial nail system which resists problems due to microbial growth.

It is therefore an object of the present invention to provide an artificial nail composition and method which does not result in greenies. A further object is to provide a composition and method for artificial nails which is easy to apply, hardens quickly and with excellent strength, is comfortable to the wearer, is durable, and has excellent cosmetic appearance.

SUMMARY OF THE INVENTION

These objects, and others which will become apparent from the following detailed description, are achieved by the present invention which in one aspect comprises a composition useful for artificial nails comprising a liquid component comprising one or more polymerizable acrylic monomers; a solid or gel component comprised of polymerization initiator catalyst and a polymer of one or more acrylic monomers; and one or more antimicrobial compounds. This invention provides a safer alternative to materials presently being used.

In another aspect the invention comprises a method of preparing such artificial nails.

Another aspect of the invention is an artificial nail prepared by such process.

An additional aspect is a method of preparing compositions useful for artificial nails.

DETAILED DESCRIPTION OF THE INVENTION AND THE PREFERRED EMBODIMENTS

I. The Liquid Component

The liquid component preferably comprises one or more polymerizable acrylic monomers, amine accelerators, and auxiliary components. Suitable monomers are any which are normally used for artificial nails, including, for example, alkyl methacrylate, hydroxy functional methacrylate, polyfunctional methacrylate, and acetoxy methacrylate.

One or more polyfunctional methacrylates (di-, tri-, and/or higher-functional) may also be included in the liquid component portion to serve as crosslinkers. These polyfunctional methacrylates serve to increase the mechanical strength of the cured polymer fingernail/coating, improving such properties as stiffness, tensile strength, abrasion resistance, and chemical resistance. The shorter chain dimethacrylates and the tri- or higher methacrylates tend to give more brittle cured polymer properties, while the longer chain dimethacrylates result in cured polymers that are tough, yet fairly flexible, and are therefore preferred. To obtain the desired cured polymer properties, careful selection of and formulation with these polyfunctional methacrylates is necessary as is known in the art.

Although any polyfunctional methacrylates or combination of polyftnctional methacrylates can be used, the following polyfunctional methacrylates have been found to be particularly useful: ethylene glycol dimethacrylate, diethylene glycol dimethacrylate, trimethylene glycol dimethacrylate, terra ethylene glycol dimethacrylate, polyethylene glycol dimethacrylate, dipropylene glycol dimethacrylate, tripropylene glycol dimethacrylate, 1,4-butanediol dimethactylate, 1,3-butanediol dimethacrylate, 1,6-hexadeciol dimethacrylate, 1,5-hexanediol dimethacrylate, neopentyl glycol dimethacrylate, t1, 12-dodecane-diol dimethacrylate, 2,2-bix [4'-(3"-methacryloy]-2"-hydroxypropoxy)-phenyl]propane (bix-GMA), 2,2-bis(4'-methacryloyl phenyl)propane (bis-phenol A dimethacrylate), ethoxylated bis-phenol A dimethacrylate, dimethacrylate-terminated aliphatic and aromatic urethanes, trimethylol-propane trimethacrylate, glycerol dimethacrylate. Sorbitol dimethacrylate, pentaerythritol tetra methacrylate, and mixtures thereof. Methacrylate terminated and/or functional polymers are also contemplated, such as the hydroxy ethyl methacrylate adducts of styrene/-maleic anhydride copolymers and methyl vinyl ether/-maleic anhydride copolymers.

Suitable acetoxy methacrylate monomers are any which have high solvency, low volatility, low toxicity, and, preferably, lack of odor, including, for example, methoxyethoxyethyl methacrylate, ethoxyethoxyethyl methacrylate, propoxyethoxyethyl methacrylate, isopropoxyethoxyethyl methacrylate, butoxyethoxyethyl methacrylate, isobutoxyethoxyethyl methacrylate, methoxyethoxymethyl methacrylate, ethoxyethoxymethyl methacrylate, acetoacetoxyethyl methacrylate, and tertiary-butoxyethoxyethyl methacrylate, and the like.

Hydroxy functional methacrylate monomers may be included in the liquid component portions so as to modify the mechanical properties of the cured polymer fingernail/coating. Preferably, those methacrylate monomers having little or no odor are included in the liquid component of the present invention, generally in an amount from about 5 percent to about 65 percent by weight of liquid component. Exemplary hydroxy methacrylate monomers are hydroxy ethyl methacrylate, hydroxy propyl methacrylate, hydroxy butyl methacrylate, glycerol mono and di methacrylates, sorbitol di, tri, and methacrylates, tetrahydrofurfuryl methacrylate, and mixtures thereof. Tetrahydrofurfuryl methacrylate possesses a mild, distinct odor, therefore limiting it's concentration in the liquid component to an amount not greater than about 20 percent by weight of liquid component. The most preferred hydroxy methacrylate monomer is hydroxy ethyl methacrylate and/or hydroxy propyl methacrylate, in an amount from about 0.5 percent to about 30 percent by weight of liquid component.

The tertiary amine accelerators are generally known in the art, and are preferably aromatic tertiary amines such as N,N-dimethyl-p-toluidine, N,N-dihydroxyethyl-p-toluidine, N,N-dimethyl aniline, and/or 4-(dimethylamino)phenethyl alcohol (U.S. Pat. No. 4,284,551). The accelerator is usually employed at a concentration of from about 0.1 percent to about 5.0 percent by weight of liquid component. The preferred tertiary amine accelerators are N,N-dimethyl-p-toluidine and N,N-dihydroxyethyl-p-toluidine.

The liquid component may optionally contain auxiliary components such as dyes, natural and synthetic polymers, polymerization inhibitors such as BHT and/or MEHQ and ultraviolet light absorbers such as 2-hydroxy-4-methoxy-benzophenone (Uvinul M-40, BASF/Wyandotte).

II. The Solid or gel Component

The solid or gel component of the compositions of the invention preferably comprises acrylic polymer and other ingredients such as pigments, secondary polymers, and/or flow modifiers, such as fumed silica. The solid or gel component is generally in the form of a finely divided powder, and generally includes a polymerization catalyst.

Preferred acrylic polymers are poly(ethyl methacrylate), poly(ethyl-co-butyl methacrylate), poly(ethyl-co-methyl methacrylate), poly(methyl-co-butyl methacrylate) and mixtures thereof. Preferred amounts of acrylic polymer are about 95 percent to about 99.5 percent, based on weight of solid or gel component. Also suitable are the so-called gel types of polymers which include acrylate and methacrylate oligomers, urethane acrylate and methacrylate oligomers, and epoxy acrylate and epoxy methacrylate oligomers.

Suitable secondary polymers may include finely divided poly(vinyl acetate), for example.

The acrylic polymer in the solid or gel component is preferably a polymer or copolymer of ethyl or methyl methacrylate. Finely divided poly(ethyl methacrylate), poly(ethyl-co-methylmethacrylate), poly(ethyl-co-butyl methacrylate), and poly(methyl-co-butyl) methacrylate) have been found to be most suitable. These finely divided polymers or copolymers are generally included in the powder portion at from about 80 percent to about 99.5 percent by weight polymeric powder.

The solid or gel component may optionally contain flow modifiers such as fumed silica and/or secondary finely divided polymers such as poly(vinyl acetate). Flow modifiers serve to adjust or modify the working properties of the admixed liquid component and polymeric power for easier manipulation. In addition, the polymeric powder may contain pigments such as titanium dioxide, and/or fillers such as hydrated alumina, finely divided glass powder, or silicon dioxide.

Suitable polymerization initiators are conventional soluble peroxide or azo initiators such as benzoyl peroxide, lauroyl peroxide, t-butyl peroxy-2-ethyl hexanoate, 2,2'-azobisisobutyronitrile or 2,2'-azobis((2,4-dimethylvaloronitrile, cumene hydroperoxide, tert-butyl hydroperoxide, dicumyl peroxide, di-tert-butyl peroxide, lauroyl peroxide, dibenzoyl peroxide, hydrogen peroxide, ammonium persulfate, potassium persulfate, sodium persulfate, metal peroxides, hyponitrous acid esters, and metal chelate compounds, barbituric acid derivatives, and the like.

Benzoyl peroxide is preferred. Preferred amounts of polymerization initiator are about 0.5 percent to about 3.0 percent, based on weight of solid or gel component. The polymerization catalyst can be combined with the other constituents of the solid or gel component in any convenient way. One preferred way of combining the polymerization catalyst is to grind it into the surface of the granular or powdered solid or gel component.

III. The Antimicrobial Component

The antimicrobial compound can comprise one or a mixture of bactericides and fungicides. Preferred among the suitable compounds used for the antimicrobial are o-benzoyl-p-chlorophenol, phenol, polyvinylpyrrolidone-iodine complex, methyl and propyl parabin, dimethyl aminoethyl methacrylate octyl quaternary compound, a mixture of methylisothiazolone and methylchloroisothiazolone, thymol, octyl isothiazalone, 10,10,oxybisphenoxarsine, miconazole, undecylenic acid, salicylic acid, tolnaftate, and cicloprix olamine. Suitable anti-fungal agents are any which are known, and are preferably anti-fungal agents selected for the group of ciclopox olamine, clotromazol, miconazole, bifonazole, and mixtures thereof.

Various methods of including the antimicrobial component in the artificial nails and artificial nail compositions of the invention are contemplated by this invention. The antimicrobial can be incorporated into the solid or gel component, the liquid component, or into both components.

To incorporate the antimicrobial into the solid or gel component, the antimicrobial can be combined during the preparation of the acrylic polymer or secondary polymer, or can be physically combined with the acrylic polymer and other components of the solid or gel component prior to finely dividing the solid or gel component. The preparation of the acrylic polymer and/or any secondary polymer is otherwise conventional, except for the inclusion of the antimicrobial. The antimicrobial does not necessarily copolymerize with the polymer, although in some cases it does copolymerize.

To incorporate the antimicrobial in the liquid component, the antimicrobial can be added to the monomer or to the liquid component itself.

Preferred amounts of antimicrobial are 0.01 to about 2.0 percent based on the total weight of the combined liquid and solid or gel components. The antimicrobial is present in the final artificial nail and functions to prevent the growth of bacteria and/or fungus which causes greenies.

IV. The Method of Preparing the Compositions

The preferred methods of preparing the compositions of the invention are either (or both) polymerizing one or more acrylic monomers in the presence of one or more antimicrobial compounds and combining the resultant polymer with the polymerization initiator catalyst to form the solid or gel component; and preparing the liquid component by mixing one or more acrylic monomers with an accelerator.

V. The Method of Forming Artificial Human Nails

The artificial fingernails of the invention are formed by mixing the liquid component and the polymeric powder component, at least one of which comprises an antimicrobial compound, and shaping the mixture while applying it to the surface of a natural nail or to a natural nail to which primer has previously been applied.

VI. Optional Primers

Fingernail primers can be based on acrylic monomers, derivatives of acrylic monomers, monomer in acetone or isopropanol, or other monomers in other solvents, or solvent alone without monomer. Both methacrylic acid and unsaturated carboxylic derivatives, such as those described in U.S. Pat. No. 4,863,993, as well as solvents and modified solvent mixtures, such as those described in U.S. Pat. No. 4,766,005 are suitable. According to the present invention, an antimicrobial can be included in the primer or preparation step of producing the artificial nail. The primer can be applied by use of a brush, tissue, towelette, or other material.

VII. The Artificial Nails

The resultant artificial nails have improved properties with respect to growth of bacteria in the interface between the artificial nail and the natural nail.

EXAMPLES

The following example is a composition that has been found to be useful in the artificial fingernail art and which incorporates an antimicrobial agent.

Example 1 (Control)

| Liquid Component | Percent by Weight |
| --- | --- |
| Ethyl methacrylate | 71.0 |
| hydroxypropyl methacrylate | 10.0 |
| 2-(methacryloyloxy) ethyl acetoacetate | 6.0 |
| tetraethylene glycol dimethacrylate | 12.0 |
| n,n-dimethyl-p-toluidine | 1.0 |
| Total | 100.00% |
| Polymeric Powder | |
| Poly (ethyl methacrylate) | 98.4 |
| Benzoyl peroxide (polymerization initiator) | 1.6 |
| Total | 100.00% |

The above components, when combined in a ratio of approximately one part liquid component to about two parts polymeric powder, result in a suitably workable slurry or dough for shaping an artificial fingernail. The shaped mass will then be observed to cure to a hard fused polymer fingernail in approximately 120 seconds from the beginning of mixing. The above control formulation, when combined, polymerizes to a highly flexible artificial fingernail material.

The following antimicrobials were used in a comparative experiment in which artificial nails were formed on human nails from materials A through J, and compared with nails formed from control composition K. In materials A–D, the antimicrobial was added to the liquid at 0.2% by weight based on total composition. In materials E–J the antimicrobial was added to the solid or gel at the same %.

| Material | Antimicrobial |
|---|---|
| A | o-benzyl-p-chlorophenol |
| B | phenol |
| C | polyvinyl pyrollidone iodine complex |
| D | methyl and propyl parabin |
| E | o-benzyl-p-chlorophenol |
| F | phenol |
| G | polyvinyl pyrollidone iodine complex |
| H | methyl and propyl parabin |
| I | dimethylaminoethyl methacrylate-octyl quat copolymer |
| J | methyl isothiazolone methylchloro-isothiazolone |
| K | control |

In a population of the following numbers of clients for the following periods of time, the following number of growths ("greenies") was observed:

| MATERIAL | # CLIENTS | # WEEKS | # GROWTHS |
|---|---|---|---|
| A | 3 | 12 | 0 |
| B | 5 | 12 | 0 |
| C | 3 | 12 | 0 |
| D | 7 | 12 | 0 |
| E | 2 | 12 | 0 |
| F | 3 | 12 | 0 |
| G | 5 | 12 | 0 |
| H | 11 | 12 | 0 |
| I | 2 | 12 | 1 |
| J | 2 | 12 | 0 |
| K (CONTROL) | 28 | 20 | 7 |

While the present invention has been described and exemplified in detail herein, it is to be appreciated that various other other embodiments should become apparent to those skilled in this art without departing from the spirit and scope of the present invention.

What is claimed is:

1. An antimicrobial artificial nail composition, wherein the composition comprises:
   (1) at least one liquid component comprising one or more polymerizable acrylic monomers;
   (2) at least one solid or gel component, comprising one or more polymerization initiator catalysts and a polymer or oligomer of one or more acrylic monomers; and
   (3) one or more antimicrobial compounds, which retain antimicrobial activity in combination with (1) and (2) above, wherein the one or more antimicrobial compounds are selected from the group consisting of o-benzoyl-p-chlorophenol, phenol, polyvinylpyrrolidone-iodine complex, methyl and propyl parabin, dimethyl aminoethyl methacrylate octyl quaternary compound, a mixture of methylisothiazolone and methylchloroisothiazolone, thymol, octyl isothiazalone, 10,10,oxybisphenoxarsine, miconazole, undecylenic acid, salicylic acid, tolnaftate, and cicloprix olamine.

2. Composition according to claim 1 wherein said liquid component is selected from the group consisting of alkyl acrylate or methacrylate, hydroxyalkyl acrylate or methacrylate, diacrylate or dimethacrylate, and acetoxyalkyl acrylate or methacrylate.

3. Composition according to claim 2 wherein the ratio of alkyl methacrylate to hydroxyalkyl methacrylate is about 2:1 to about 20:1 by weight.

4. A composition according to claim 2 wherein said alkyl acrylate or methacrylate is ethyl methacrylate, said hydroxyalkyl acrylate or methacrylate is selected from the group consisting of hydroxyethyl methacrylate and hydroxypropyl methacrylate, said diacrylate or dimethacrylate is selected from the group consisting of ethylene glycol dimethacrylate, ethylene glycol trimethacrylate, and ethylene glycol tetramethacrylate, and said acetoxyalkyl methacrylate is ethoxyethyl methacrytate or acetoacetoxy methacrylate or ethoxyethyl methacrylate and acetoacetoxy methacrylate combined.

5. Composition according to claim 1 wherein said solid or gel component is comprised of an alkyl acrylate or methacrylate polymer physically admixed with a peroxide polymerization initiator.

6. Composition according to claim 1 wherein said solid or gel component is a UV curable gel comprising urethane or epoxy acrylate oligomer.

7. Composition according to claim 1 wherein said solid or gel component comprises a UV curable gel selected from the group consisting of urethane acrylate oligomer, urethane methacrylate oligomer, epoxy acrylate oligomer, polyester acrylate oligomer, aromatic acid oligomer, alkylcyanoacrylate, polyalkylcyanoacrylate, and epoxy methacrylate oligomer.

8. Composition according to claim 1 wherein said solid or gel component is a polymer or copolymer of ethyl methacrylate with benzoyl peroxide ground on the surface thereof.

9. Composition according to claim 1 wherein said antimicrobial compound comprises about 0.001 to about 1.0 percent of the total weight of said liquid component and said solid or gel component.

10. Composition according to claim 1 wherein said antimicrobial compound is present in said liquid component.

11. Composition according to claim 1 wherein said antimicrobial compound is present in said solid or gel component.

12. Composition according to claim 1 wherein said antimicrobial compound is mixed with the monomer mixture from which the solid or gel component is polymerized.

13. Composition according to claim 1 wherein said antimicrobial compound is present in both said liquid component and said solid or gel component.

14. Composition according to claim 1 wherein said liquid component comprises alkyl methacrylate, hydroxyalkyl methacrylate, a dimethacrylate, acetoacetoxy ethyl methacrylate, and an amine accelerator; and said solid or gel component comprises an acrylic polymer, antimicrobial compound, and benzoyl peroxide.

15. The composition according to claim 1, wherein
   (A) the liquid component comprises:
      (1) one or more acrylic monomers selected from the group consisting of ethyl methacrylate, hydroxyethyl methacrylate, ethylene glycol dimethacrylate, hydroxypropyl methacrylate, acetoacetoxy ethyl methacrylate and ethoxyethyl methacrylate, and
      (2) an amino accelerator compound;
   (B) the solid or gel component comprises an acrylic polymer;

(C) the antimicrobial component is selected from the group consisting of o-benzoyl-p-chlorophenol, phenol, polyvinylpyrrolidone-iodine complex, methyl parabin, propyl parabin, dimethyl aminoethyl methacrylate octyl quaternary compound, and a methylisothiazolone/methylchloroisothiazolone mixture; and (D) the initiator catalyst is benzoyl peroxide.

16. A method of preparing a composition of claim 1 comprising one or more polymerizing acrylic monomers in the presence of one or more antimicrobial compounds and combining the resultant polymer with the polymerization initiator catalyst to form the solid or gel component; and preparing the liquid component by mixing one or more acrylic monomers with an accelerator.

17. A method of forming of forming an artificial human nail comprising providing a composition according to claim 1, mixing the at least one liquid component with the at least one solid or gel component, and the one or more antimicrobial compounds, applying the mixture to the surface of an existing human or artificial nail surface, shaping the mixture to a desired form, and allowing the mixture to polymerize and harden.

18. An artificial nail prepared according to the method of claim 15.

19. A method of using the composition of claim 1 as an artificial nail preparation or nail primer comprising an antimicrobial compound.

* * * * *